United States Patent [19]

Jolles et al.

[11] 4,110,434
[45] Aug. 29, 1978

[54] NOVEL IMMUNOLOGICAL ADJUVANTS, PROCESS FOR THEIR PRODUCTION AND COMPOSITIONS CONTAINING THEM

[75] Inventors: Pierre Jolles, Paris; Daniéle Migliore-Samour, Kremlin-Bicetre, both of France

[73] Assignee: Agence Nationale de Valorisation de la Recherche (ANVAR), Neuilly sur Seine, France

[21] Appl. No.: 711,193

[22] Filed: Aug. 3, 1976

[30] Foreign Application Priority Data

Aug. 5, 1975 [FR] France .................................. 75 24440

[51] Int. Cl.² .................... A61K 39/02; C07C 103/52; A61K 37/00
[52] U.S. Cl. .............................. 424/92; 260/112.5 R; 424/177
[58] Field of Search ................. 260/112.5 R; 424/177, 424/92

[56] References Cited

U.S. PATENT DOCUMENTS

| 3,429,868 | 2/1969 | Kominati | 260/112.5 R |
| 3,941,762 | 3/1976 | Parker | 260/112.5 R |
| 3,956,481 | 5/1976 | Jolles et al. | 195/96 |
| 3,992,528 | 11/1976 | Graham et al. | 424/177 |
| 4,013,788 | 3/1977 | Jolles et al. | 424/92 |

FOREIGN PATENT DOCUMENTS 28,16V 6/1972 Netherlands .................... 260/112.5 R

OTHER PUBLICATIONS

Biochem. & Biophys. Res. Comm. 26, (1967), pp. 492-496.

*Primary Examiner*—Delbert R. Phillips
*Attorney, Agent, or Firm*—Burgess, Dinklage & Sprung

[57] ABSTRACT

Novel derivatives with immunological activity are obtained by reacting a hydrosoluble extract of mycobacteria with an aliphatic acid derivative containing 10 to 18 carbon atoms and isolating the resulting product. The hydrosoluble extract of mycobacteria is a tetrasaccharide-heptapeptide or its dimer, trimer or tetramer possibly associated with non-amino reducing sugars. The derivative has the formula:

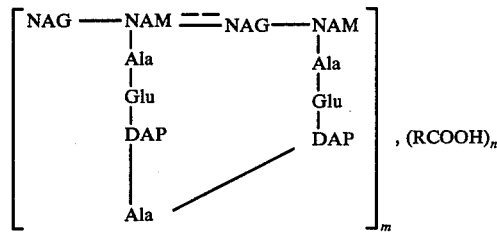

in which $m$ is a whole number comprised between 1 and 4 inclusive, $n$ is a whole number at least equal to 1 and R is an alkyl radical containing 9 to 17 carbon atoms.

18 Claims, 4 Drawing Figures

NOVEL IMMUNOLOGICAL ADJUVANTS, PROCESS FOR THEIR PRODUCTION AND COMPOSITIONS CONTAINING THEM

BACKGROUND OF THE INVENTION

1. Field of the Invention

The present invention relates to new immunological adjuvants, more particularly derivatives of hydrosoluble extracts of mycobacteria, and to a process for their production. The invention also relates to pharmaceutical compositions containing said derivatives obtained from hydrosoluble extracts of mycobacteria.

2. Description of the Prior Art

It is known that the hydrosoluble part of "D waxes" of mycobacteria, currently named "Poly PA" possess adjuvant activity. Methods have already been described for the extraction of this hydrosoluble part of mycobacteria, notably by chemical processing, by enzymatic processing or by homogenization or acetylation.

In Belgian Patent No. 801,016 there are described hydrosoluble extracts of mycobacteria whose molecular weight is comprised between 3,500 and 30,000. They possess a non-arthrogenic adjuvant activity when they are added to a mineral oil (Freund's incomplete adjuvant).

These hydrosoluble extracts are constituted essentially from a mixture in variable proportions of hydrosoluble fragments of the cell wall, possibly associated with non-amino reducing sugars. The hydrosoluble fragments of the cell wall are constituted essentially by a tetrasaccharide-heptapeptide and by its dimer, trimer and tetramer.

The tetrasaccharide-heptapeptide of the cell wall has the following molecular composition: N-acetylglucosamine (2), N-acetylmuramic acid (2), alanine (3), glutamic acid (2), $\alpha,\alpha'$-diaminopimelic acid (2), and its skeleton can be represented by the following diagram:

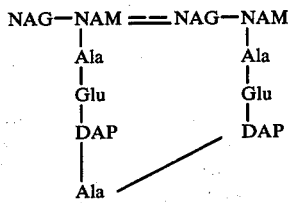

NAG: N-acetylglucosamine
NAM: N-acetylmuramic acid
Ala: alanine
Glu: glutamic acid
DAP: $\alpha,\alpha'$-diaminopimelic acid Between two NAG-NAM units, it is possible to have, either the presence of a covalent linkage, or the total absence of a linkage; in the latter case, the linkage of the whole is ensured by the peptide portion.

OBJECTS AND SUMMARY OF THE INVENTION

It is an object of the invention to provide novel immunological adjuvants for the production of antibodies and the potentiation of delayed hypersensitivity, non-arthrogenic and capable of acting alone, that is to say without it being necessary to administer them in an oily solution.

It is another object of the invention to provide a process for the production of said novel immunological adjuvants from hydrosoluble extracts of mycobacteria.

It is a further object of the present invention to provide novel pharmaceutical compositions containing at least one said novel immunological adjuvant.

It is another object of the invention to provide a process for the production of novel pharmaceutical compositions containing at least one of said novel immunological adjuvants.

A further object of the invention is to provide an improved method of treating bacterial, viral, parasitic and allergenic disorders by means of antigens of diverse natures by the concurrent administration of said novel immunological adjuvants either alone or in association with said antigens.

Other objects and features of the invention will become apparent from the description which follows.

According to the present invention there are provided novel compounds constituted from hydrosoluble extracts of mycobacteria, coupled with long chain aliphatic acids containing 10 to 18 carbon atoms, that is to say from a tetrasaccharide-heptapeptide and/or its dimer, trimer, tetramer of the cell wall of the mycobacteria, comprising long chain aliphatic acid residues, said tetrasaccharide-heptapeptide or its dimer, trimer or tetramer being possibly associated with non-amino reducing sugars, such as, for example, mannose, glucose, galactose or arabinose.

The derivatives obtained from hydrosoluble extracts of mycobacteria according to the invention may be represented diagrammatically by the following formula:

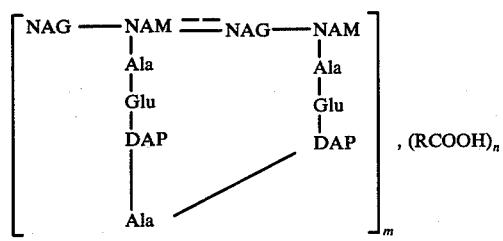

in which $m$ is a whole number comprised between 1 and 4 inclusive, $n$ is a whole number at least equal to 1 and R is an alkyl radical containing 9 to 17 carbon atoms.

According to another aspect of the present invention, the new immunological adjuvants can be prepared by the action of a derivative of an aliphatic acid containing 10 to 18 carbon atoms on hydrosoluble extracts of mycobacteria, obtained for example, according to the processes described in the above-mentioned Belgian patent no 801,016, namely by the homogenisation in water or by extraction with pyridine or by acetylation of delipidised bacterial residues of mycobacteria.

The acid or its derivatives react on the free amino functions of the tetrasaccharide-heptapeptide to form amide linkages —CO—NH— and on the hydroxylated functions of the sugars to form ester linkages —CO—O—.

The hydrosoluble extracts applied in the process of the invention can come from any mycobacteria of human or non-human origin, virulent or non-virulent, which contains a "D wax". By way of example of such mycobacteria may be mentioned *Mycobacterium tuberculosis*, var.hominis strain $H_{37}Ra$, Test strain, Brevannes strain, Peurois strain, *Mycobacterium kansasii, Mycobacterium tuberculosis,* var.bovis, LA and BB strains, Behring strain, Mycobacterium phlei, etc.

The acid whose derivative is applied in the process according to the invention corresponds to the formula RCOOH, in which R is as previously defined. By way of example of long chain aliphatic acids, whose derivatives are suitable for the purposes of the invention, may be mentioned: palmitic acid, lauric acid, etc. . .

The aliphatic acid derivative applied is advantageously the anhydride or an acid halide.

When an acid anhydride is used, the operation is carried out in an organic solvent, such as tertiary butyl alcohol advantageously at ambient temperature, at a pH of about 9 and in the presence of an excess of the acid anhydride.

When an acid halide is used, preferably the acid chloride, the operation is carried out in an anhydrous basic organic solvent, such as pyridine, at a temperature comprised between 0° and 5° C., in the presence of an excess of acid chloride in an anhydrous organic solvent, such as tetrahydrofurane, and keeping the pH at a value above 8.

The compounds according to the invention are then isolated from the reaction medium, for example by precipitation, evaporation of the solvents or by any other suitable means.

The novel compounds obtained according to the process of the present invention can be, if necessary, purified by physical methods currently used for purification, such as precipitation, dialysis, chromatography, filtration over various supports currently used for this purpose.

The compounds according to the present invention are, as has been previously indicated, immunological adjuvants in the production of antibodies and in the potentiation of delayed hypersensitivity, non-arthrogenic, capable of acting alone, that is to say, without the necessity of administering them in oily solution.

The compounds according to the invention exert, when they are administered in aqueous solution, a significant adjuvant power which is distinctly more marked than that of the hydrosoluble extracts from which they are derived, this adjuvant power being determined by the ovalbumin hypersensitivity test in the guinea pig (according to the principle of the method of R. G. White et al. Immunology, 7, 158 (1964)) and by the production of circulating antibodies against influenzal antigens in the rabbit.

Moreover, it should be noted that the compounds according to the invention only display a low toxicity; in fact, in the mouse, the compounds according to the invention, at the dose of 25 mg/kg administered by the intravenous route, cause neither loss of weight, nor mortality, nor hypertrophy of the spleen or of the liver, nor sensitization to endotoxins.

According to another aspect of the present invention there are also provided pharmaceutical compositions which contain at least one compound according to the invention in association with one or several compatible diluents or excipients. These compositions can be used alone or in association with antigens of various types (bacterial, viral, parasitic or allergenic) in order to increase the immunitary response with respect to these antigens.

In these compositions, the content of the compound according to the invention is generally higher than 0.1% by weight of the total composition. These compositions can be used by the oral, rectal or parenteral route or in aerosols.

In human therapeutics, the doses depend on the desired action. They can be comprised between 10 and 50 mg per day of the novel compound in the adult.

The invention will be more fully understood by means of the supplementary description and examples which follow, with reference to the accompanying drawings, given, of course, purely by way of non-limiting illustration.

BRIEF DESCRIPTION OF THE DRAWINGS

In the drawings, which relate to specific embodiments of the invention.

DESCRIPTION OF SPECIFIC EMBODIMENTS

Example 1

30 mg of hydrosoluble extract, obtained from *Mycobacterium tuberculosis,* var.hominis, $H_{37}Ra$ (no ATCC) 25177) having a molecular weight of 14,000 ± 2,000 were dissolved in 3 $cm^3$ of a pH 9.5 buffer of sodium carbonate in tertiary butyl alcohol (obtained from 7 volumes of an aqueous solution of 0.5 M sodium carbonate and from 3 volumes of tertiary butyl alcohol). In 5 minutes, with stirring, there was added lauric anhydride in solution in tertiary butyl alcohol (in the proportion of 40 moles of lauric anhydride in 0.5 $cm^3$ of tertiary butyl alcohol per mole of hydrosoluble extract employed). The stirring was continued for 30 minutes at 20° C., then 80% tertiary butyl alcohol was added. The precipitate which formed was separated by centrifugation. The precipitate was washed with pure tertiary butyl alcohol. After another centrifugation and washing with tertiary butyl alcohol, the precipitate was dissolved in water and the resulting solution was dialysed against distilled water. The solution which did not dialyse was lyophilised. In this way 25 mg of coupled product was obtained whose characteristics were as follows:

composition in amino acids: alanine (3), glutamic acid (2), α,α'-diaminopimelic acid (2)

content of alanine: 1.5%

Figure 1:
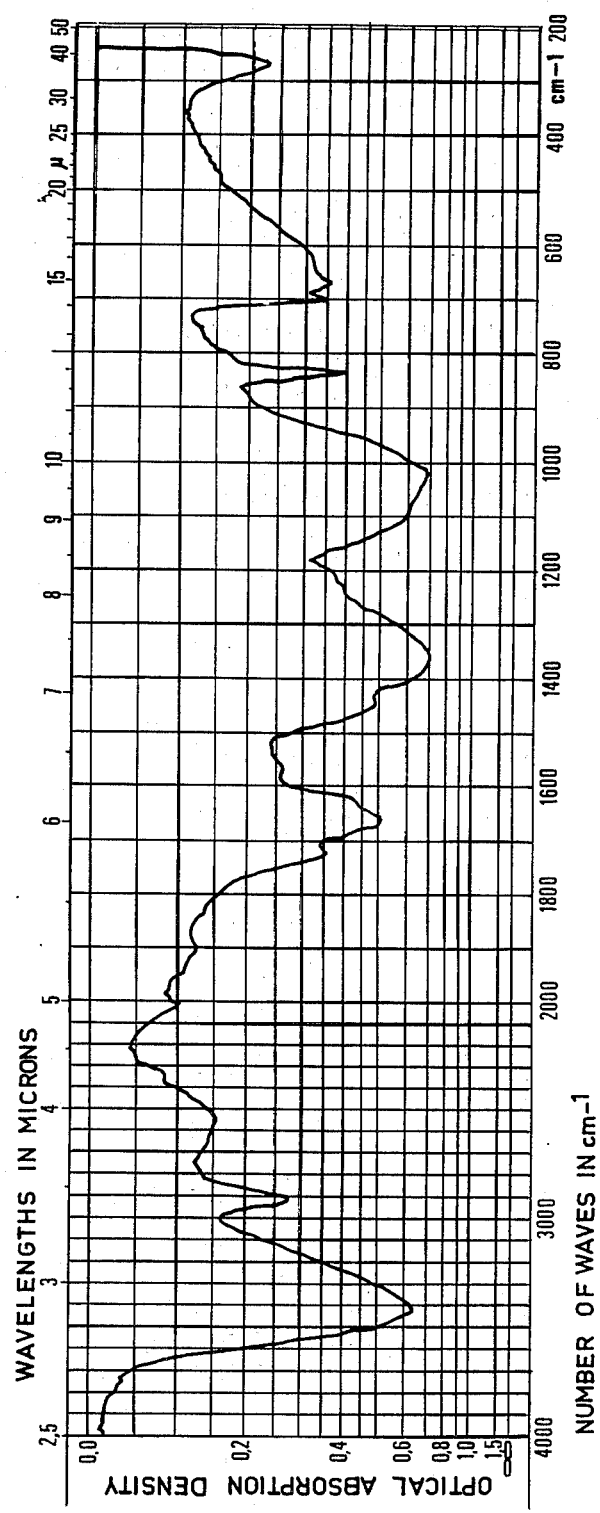
FIG. 1 shows an infrared spectrum of one embodiment of a product according to the invention.

The product thus obtained is further characterised by its infrared spectrum shown in FIG. 1 which was determined from tablets of said product in admixture with KBr.

Figure 2:
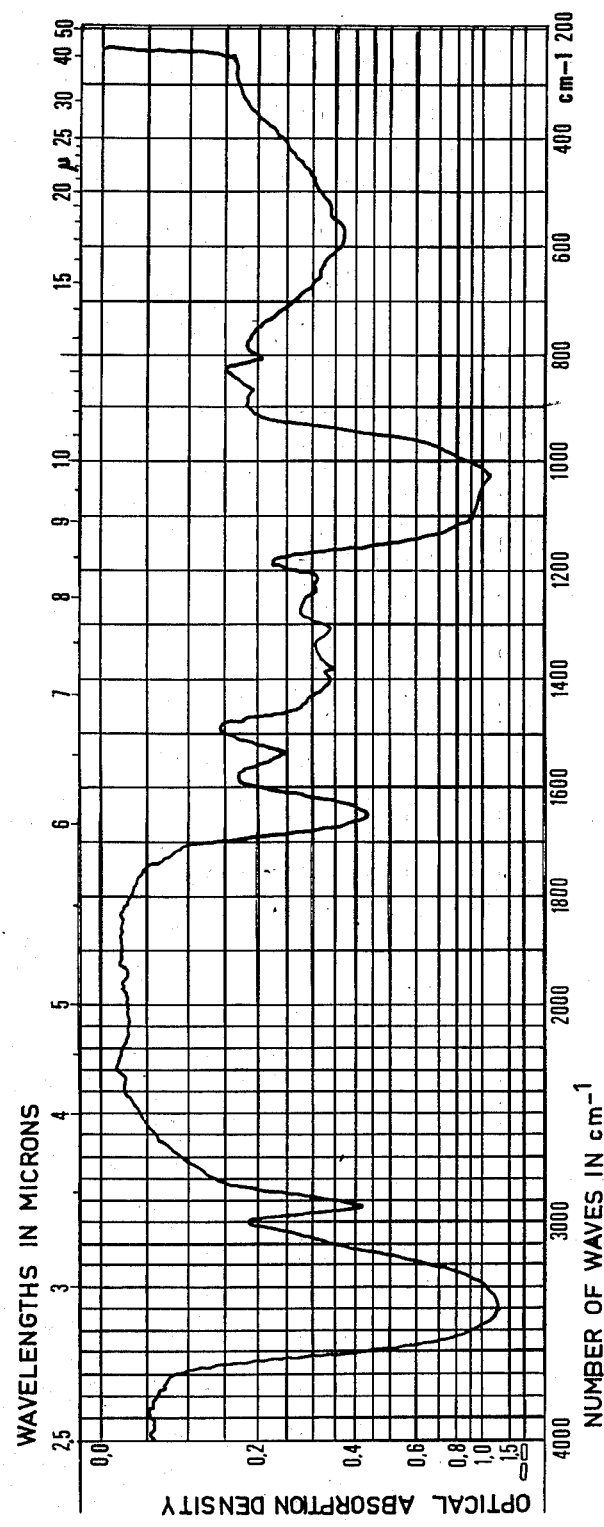
FIG. 2 shows an infrared spectrum of the starting material for the embodiment of FIG. 1.
Figure 3:
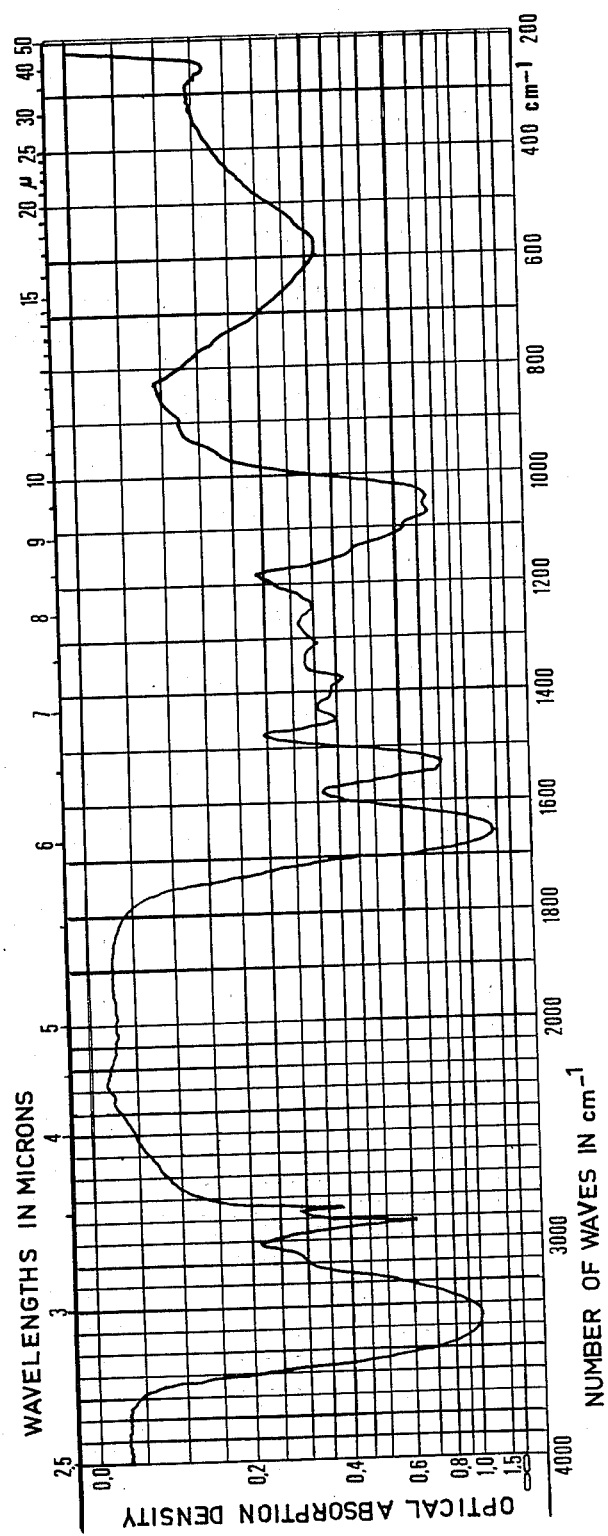
FIG. 3 shows an infrared spectrum of another embodiment of a product according to the invention; and, FIG. 4 shows an infrared spectrum of the starting material for the embodiment of FIG. 3.
Figure 4:
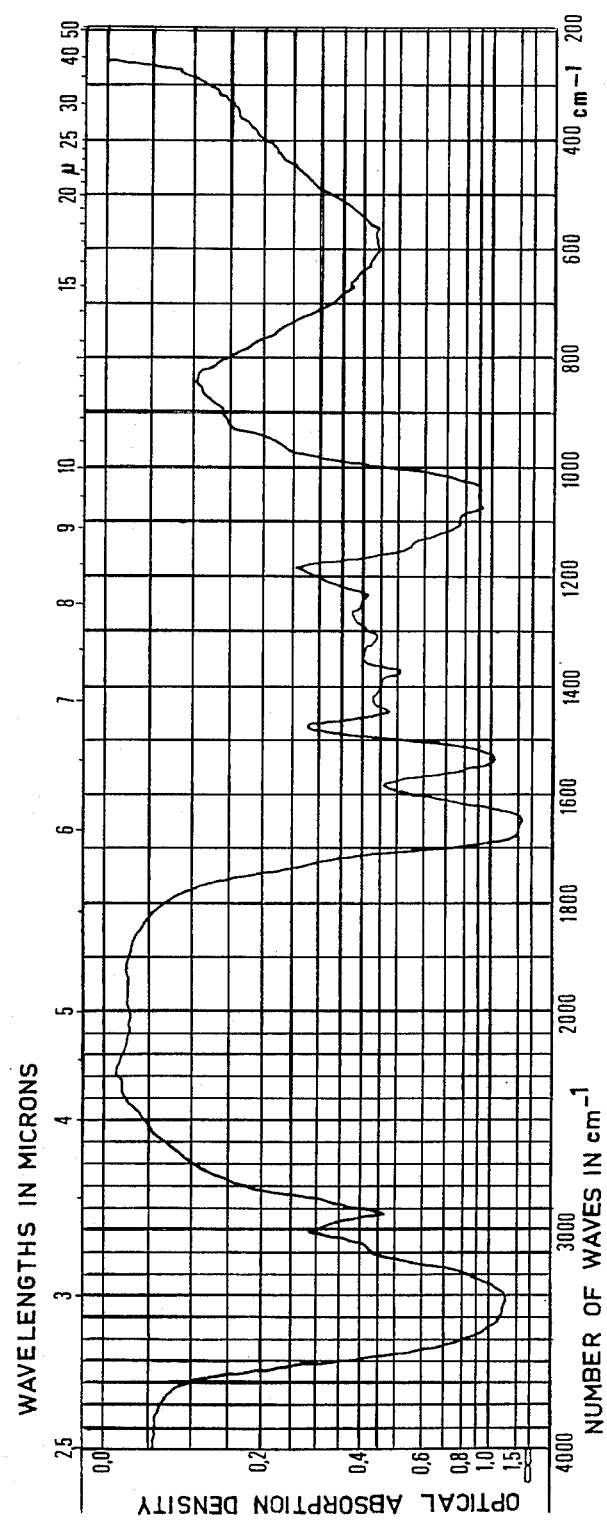

FIG. 2 shows the spectrum of the starting product recorded under the same conditions, that is to say, of the hydrosoluble extract of *Mycobacterium tuberculosis,* var.hominis, $H_{37}R_a$.

The hydrosoluble extract of mycobacteria used as starting material in this Example was prepared by the following operational procedure:

100 g of bacterial residue, obtained from *Mycobacterium tuberculosis* var.hominis, strain $H_{37}Ra$, were ground and homogenised in 500 $cm^3$ of water by means of a grinder of the "Ultra-Turrax" type.

After having been stirred for 24 hours at 20° C. and centrifuged the resulting product for 30 minutes at 4° C. (4,000 rpm), the supernatant layer was heated to 80° C.

Ammonium sulfate was then added so as to obtain a 40% saturated solution. After 12 hours at 4° C. and centrifugation for 30 minutes, a precipitate ($P_{40}$) was obtained.

To the supernatant layer, ammonium sulfate was added so as to obtain a 70% saturated solution. After 12 hours at 4° C. and centrifugation for 30 minutes under the same conditions, a precipitate ($P_{70}$) was obtained.

The last supernatant layer ($S_{70}$) was dialysed against distilled water. The solution which did not dialyse was lyophilised. The product thus obtained was purified by chromatography over DEAE-cellulose equilibrated with a Veronal buffer, 0.05 M HCl at pH 7 eluting therefrom with a 0.05 M sodium citrate buffer at pH 3. The purified product was then filtered on the material known commercially as "Biogel $P_{10}$", eluting therefrom with 0.01 M acetic acid. The hydrosoluble extract thus obtained had the following characteristics:

molecular weight: 14,000 ± 2,000 composition of amino acids: alanine (3), glutamic acid (2), $\alpha,\alpha'$-diaminopimelic acid (2).

alanine content: 1.75%

Example 2

25 mg of hydrosoluble extract of *Mycobacterium tuberculosis* var.hominis, Test strain, of molecular weight 2900 ± 200 were homogenised in 1.5 $cm^3$ of anhydrous pyridine. Palmitoyl chloride in solution in anhydrous tetrahydrofurane (in the proportion of 15$\mu$ moles of palmitoyl chloride per 1$\mu$ mole of hydrosoluble extract) was added drop by drop, keeping the pH at a value above 8 by the addition of trimethylamine and keeping the temperature at 5° C. Stirring followed for 30 minutes at 20° C. The medium was acidified to pH 3 by the addition of a 6N hydrochloric acid. 30 $cm^3$ of water were then added. After evaporation of the solvents under reduced pressure (15 mm of mercury), the aqueous solution was filtered on a membrane known commercially as "DIAFLO $UM_2$" (sold by AMICON). The filtrate was lyophilised. 19 mg of coupled product was thus obtained whose characteristics were as follows:

molecular weight: 3300 ± 200 alanine content: 7.6%

The product was also characterised by its infrared spectrum which is shown in FIG. 3; the latter was recorded from tablets of the said product in admixture with KBr. (FIG. 4 shows the spectrum of the starting material recorded under the same conditions).

The hydrosoluble extract, used as starting material in this example was prepared according to the following operational method:

20 g of bacterial residue obtained from *Mycobacterium tuberculosis,* var.hominis, Test strain were ground and homogenised in 100 $cm^3$ of water by means of a "Ultra-Turrax" grinder.

After having been stirred for 48 hours at 40° C. and centrifuged for 30 minutes at 4° C. (4,000 rpm), the supernatant layer was heated to 80° C. Ammonium sulfate was then added so as to obtain a 40% saturated solution. After 12 hours at 4° C. and centrifugation for 30 minutes, a precipitate ($P_{40}$) was obtained.

To the supernatant layer, ammonium sulfate was added so as to obtain a 70% saturated solution.

After 12 hours at 4° C. and centrifugation for 30 minutes, under the same conditions, a precipitate ($P_{70}$) was obtained.

The last supernatant layer ($S_{70}$) was filtered on a membrane known commercially as "DIAFLO $UM_2$" (AMICON). The fraction retained was lyophilised. The product thus obtained was chromatographed on "DEAE-cellulose" equilibrated with a Veronal buffer, 0.05 M hydrochloric acid at pH 7 eluting therefrom with a 0.05 M sodium citrate buffer at pH 3. Two hydrosoluble fractions similar to substance B (high molecular weight) and to substance C (low molecular weight) described in Belgian Pat. No. 801,016, were thus obtained.

The low molecular weight fraction was purified by filtration on polyacrylamide resin known commercially as "BIOGEL $P_{10}$" then on "BIOGEL $P_4$" resin eluting therefrom with 0.01 M acetic acid. The hydrosoluble extract whose characteristics are as follows:

molecular weight: 2,900 ± 200 alanine content: 9.3% was thus obtained.

We claim:

1. A novel derivative with immunological adjuvant activity obtained from hydrosoluble extracts of mycobacteria, with or without non-amino reducing sugars associated therewith, said derivative having the formula:

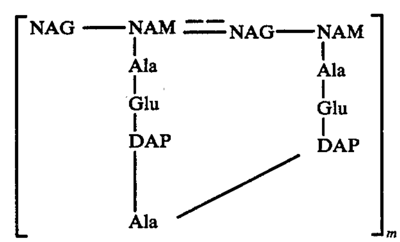

, $(RCOOH)_n$ in which *m* is a whole number between 1 and 4 inclusive, *n* is a whole number at least 1 and R is an alkyl radical containing 9 to 17 carbon atoms.

2. Novel derivative according to claim 1, wherein R is a lauryl or a palmitoyl radical.

3. Process for producing novel derivatives with immunological adjuvant acitvity according to claim 1, comprising reacting a hydrosoluble extract of mycobacteria with an aliphatic acid derivative containing 10 to 18 carbon atoms and isolating the resulting product, said hydrosoluble extract of mycobacteria being constituted by a tetrasaccharide-heptapeptide or its dimer, trimer or tetramer, with or without non-amino reducing sugars associated therewith, said tetrasaccharide-heptapeptide being represented diagrammatically by the formula:

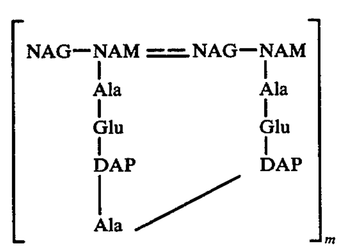

*m* being comprised between 1 and 4.

4. Process according to claim 3, wherein the hydrosoluble extract of mycobacteria employed is obtained by homogenisation in an aqueous medium by acetylation or by extraction with pyridine of delipidated bacterial residues of mycobacteria.

5. Process according to claim 4, wherein the hydrosoluble extract of mycobacteria comes from a mycobacteria containing a "D wax".

6. Process according to claim 5, wherein the hydrosoluble extract employed comes from *Mycobacterium tuberculosis*, var.hominis, $H_{37}R_a$ strain, Test strain, Brevannes strain, Peurois strain, *Mycobacterium kansasii, Mycobacterium tuberculosis*, var.bovis, LA and BB strain, Behring strain or *Mycobacterium phlei*.

7. Process according to claim 3, wherein the acid derivative employed is the acid anhydride or one of its halides.

8. Process according to claim 7, wherein the halide is the acid chloride.

9. Process according to claim 3, wherein use is made of a hydrosoluble extract of *Mycobacterium tuberculosis*, var.hominis, strain $H_{37}R_a$, having a molecular weight of 14,000 ± 2,000 and the acid derivative is lauric anhydride, the resulting derivative having the following composition in amino acids: alanine (3), glutamic acid (2), $\alpha,\alpha'$-diaminopimelic acid and a content of 1.5% by weight of alanine.

10. Process according to claim 3, wherein a hydrosoluble extract of *Mycobacterium tuberculosis*, var.hominis, Test strain, having a molecular weight of 2,900 ± 200 is used and the acid derivative is palmitoyl chloride, the resulting derivative having a molecular weight of 3,300 ± 200 and a content of 7.6% by weight of alanine.

11. A pharmaceutical composition containing an effective content of a derivative with immunological adjuvant activity according to claim 1 and at least one compatible diluent or excipient.

12. A pharmaceutical composition according to claim 11, including an antigen.

13. Method of treating bacterial, viral, parasitic or allergenic disorders in animals, by means of antigens, comprising administering an effective amount of the product according to claim 1 to said animal, either alone or in association with said antigen.

14. Method of treating disorders in human patients according to claim 13, comprising administering a dose between about 10 mg and about 50 mg per day to the patient.

15. A novel derivative of claim 1 with non-amino reducing sugars associated therewith.

16. A novel derivative of claim 1 without non-amino reducing sugars associated therewith.

17. A process of claim 3 where the hydrosoluble extract of mycobacteria contains non-amino reducing sugars associated therewith.

18. A process of claim 3 wherein the hydrosoluble extract of mycobacteria does not contain non-amino reducing sugars associated therewith.

* * * * *